(12) United States Patent
Ward et al.

(10) Patent No.: US 7,896,960 B2
(45) Date of Patent: Mar. 1, 2011

(54) METHOD OF PROTECTING WOOD THROUGH ENHANCED PENETRATION OF WOOD PRESERVATIVES AND A RELATED SOLUTION

(75) Inventors: Hans A. Ward, Wexford, PA (US); Cameron Scott, Rotorua (NZ)

(73) Assignee: Kop-Coat, Inc., Pittsburgh, PA (US)

( * ) Notice: Subject to any disclaimer, the term of this patent is extended or adjusted under 35 U.S.C. 154(b) by 280 days.

(21) Appl. No.: 12/236,044

(22) Filed: Sep. 23, 2008

(65) Prior Publication Data

US 2009/0088481 A1 Apr. 2, 2009

Related U.S. Application Data

(62) Division of application No. 11/135,770, filed on May 24, 2005, now Pat. No. 7,655,281.

(51) Int. Cl.
*A01N 33/08* (2006.01)
*A01N 33/12* (2006.01)
*A01N 25/00* (2006.01)

(52) U.S. Cl. .............. 106/18.32; 106/15.05; 106/18.29; 106/18.3; 424/405; 514/644

(58) Field of Classification Search .............. 106/15.05, 106/18.29, 18.3, 18.32; 514/644; 424/405
See application file for complete search history.

(56) References Cited

U.S. PATENT DOCUMENTS

| | | | |
|---|---|---|---|
| 4,879,083 A | 11/1989 | Knudson et al. | |
| 4,950,685 A | 8/1990 | Ward | |
| 5,468,284 A | 11/1995 | Sturm | |
| 5,763,338 A | 6/1998 | Sean | |
| 5,833,741 A | 11/1998 | Walker | |
| 5,846,305 A | 12/1998 | Payzant | |
| 5,855,817 A | 1/1999 | Walker | |
| 5,972,266 A | 10/1999 | Fookes et al. | |
| 6,235,403 B1 | 5/2001 | Vinden et al. | |
| 6,274,199 B1 | 8/2001 | Preston et al. | |
| 6,340,384 B1 | 1/2002 | Walker | |
| 6,375,727 B1 | 4/2002 | Walker | |
| 6,416,789 B1 | 7/2002 | Marks et al. | |
| 6,448,279 B1 | 9/2002 | Tseng et al. | |
| 6,485,790 B2 | 11/2002 | Walker | |
| 6,503,869 B1 | 1/2003 | Beste et al. | |
| 6,508,869 B2 | 1/2003 | Tseng et al. | |
| 6,527,981 B1 | 3/2003 | Tseng et al. | |
| 6,572,788 B2 | 6/2003 | Walker | |
| 6,582,732 B1 | 6/2003 | Bender et al. | |
| 6,811,731 B2 | 11/2004 | Archer et al. | |
| 2002/0061366 A1 | 5/2002 | Walker et al. | |
| 2002/0065206 A1 | 5/2002 | Tseng et al. | |
| 2004/0248973 A1 | 12/2004 | Ross et al. | |
| 2006/0128773 A1 * | 6/2006 | Jones ......................... | 514/373 |

* cited by examiner

*Primary Examiner*—Anthony J Green
(74) *Attorney, Agent, or Firm*—Eckert Seamans Cherin & Mellott, LLC; Arnold B. Silverman, Esquire

(57) ABSTRACT

A method of protecting wood through enhanced penetration of wood preservatives includes providing a solution including (a) at least one amine oxide, (b) at least one organic wood preservative and (c) a buffering agent. The solution preferably has a pH of about 7 to 10. The solution is applied to the surface of the wood after which, with or without intervening storage, the materials are activated to effect enhanced penetration of the organic wood preservative into the wood. One may effect application at a solution temperature of about 30 to 75° C. and preferably about 50 to 60° C. to effect activation at a higher temperature and high relative humidity. In a preferred practice, the wood may be heated before and/or after application of the solution. The solution is also disclosed as a product.

20 Claims, 1 Drawing Sheet

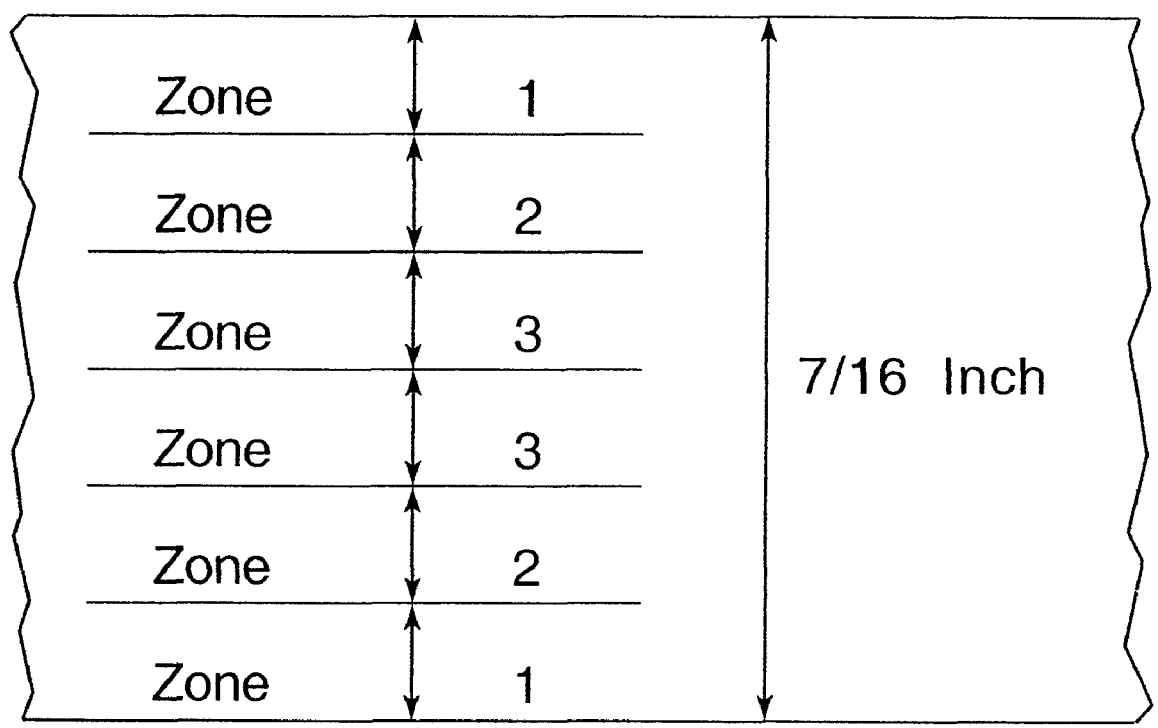
Figure

METHOD OF PROTECTING WOOD THROUGH ENHANCED PENETRATION OF WOOD PRESERVATIVES AND A RELATED SOLUTION

CROSS REFERENCE TO RELATED APPLICATION

This application is a divisional of U.S. patent application Ser. No. 11/135,770, filed May 24, 2005, and entitled "Method of Protecting Wood Through Enhanced Penetration of Wood Preservatives and Related Solution," now U.S. Pat. No. 7,655,281 which is herein incorporated by reference in its entirety.

BACKGROUND OF THE INVENTION

1. Field of the Invention

The present invention relates to an improved method of effecting enhanced penetration of wood preservatives into wood and, more specifically, it relates to such a method which contains a buffered compound which facilitates enhanced penetration of wood preservatives into the wood.

2. Description of the Prior Art

It has been known for many years to treat wood with materials which will protect the wood from deterioration. Among such approaches have been surface painting or the use of materials which will penetrate into the wood as by pressure impregnation or vacuum application. Among the materials used are fungicides, insecticides, decay-resisting materials, stain-resisting materials, weather proofing materials and others. See, for example, U.S. Pat. Nos. 4,879,083; 4,950,685; 5,468,284; 5,763,338; 5,833,741; 5,855,817; 5,972,266; 6,416,789 and 6,582,732.

In pressure and vacuum methods, the wood is treated with water or solvents that carry preservatives. The pressure or vacuum methods cause the wood to pick up large amounts of these carriers and, as a result, require kiln drying or oven drying or long-term air drying to allow the wood to be useful. Such drying of pressure or vacuum-treated wood using water as a carrier can cause structural defects such as warping, cracking and checking.

It has been known to suggest the use of amine oxides in combination with other materials in wood preservatives. See, for example, U.S. Pat. Nos. 6,274,199; 6,375,727; 6,448,279 and 6,527,981.

It has also been known to introduce into woods materials for fire-retardant properties. U.S. Pat. No. 6,811,731 discloses fire retardant protection achieved by treating green wood with a phosphate/borate.

It has also been known to suggest the combination of an amine oxide with a boron compound with the boron compound employed in a large enough amount to function as a preservative in wood. See U.S. Pat. No. 5,846,305 and United States Published Patent Application 20020065206, now U.S. Pat. No. 6,508,869.

In the use of known prior art systems which required pressure impregnation or vacuum, capital investment for the equipment needed to achieve the desired pressure relationship influenced the economics of introduction of wood-preservative materials. Also, some prior art systems employed volatile solvents which presented environmentally undesirable conditions. In addition, such solvents added to the cost of such procedures. An example of such undesirable materials are petroleum distillates.

There remains, therefore, a very real and substantial need for an improved means of effectively achieving the desired level of penetration in wood preservatives while having favorable economic aspects and avoiding risks to human health and environmentally undesirable conditions.

SUMMARY OF THE INVENTION

The present invention has met the hereinbefore described needs.

The method of the present invention permits enhanced penetration of wood preservatives through the use of solutions having a buffered pH above the pH of the wood achieved through the use of a combination of an amine oxide and a buffering agent.

In a preferred practice of the method, a solution is created with at least one amine oxide along with the wood preservative which is to be applied to the wood and a buffering agent. This solution has a pH of about 5 to 12.4 and preferably about 7 to 10 and most preferably about 7 to 8.5. It is applied to the surface of the wood. With or without intervening storage, activation results in the amine oxide and the buffering agent in the solution combining to enhance penetration into the wood of one or more wood preservatives. It is preferred that the application be at a solution temperature of about 30 to 75° C. and that the activation be at a higher temperature in a high relative humidity environment. The wood may also be heated before and/or after application of the solution to enhance penetration.

When a plurality of wood preservatives are employed, the depth of penetration of each may be to a different level, but, in general, would be enhanced as compared with introduction of the wood preservatives without the combination of the buffering agent and amine oxide present.

It is an object of the present invention to provide an improved method for enhancing depth of penetration into wood of wood preservatives.

It is another object of the present invention to provide such a method which does not require the use of pressure impregnation, vacuum systems or undesirable, volatile materials.

It is another object of the present invention to eliminate the redrying step required in prior art pressure and vacuum methods wherein water or a solvent carried the preservatives.

It is yet another object of the invention to provide such a method which can be employed on "green" lumber, i.e. lumber which contains undried sap or other green wood-based products in order to enhance penetration.

It is yet another object of the present invention to provide such a method wherein the wood to which the solution of the present invention has been applied may be stored for a significant period of time prior to a further activation stage.

It is a further object of the present invention to provide a solution for use in the method of the invention or a concentrate containing some or all of the desired compounds which can be diluted to create the desired solution with or without the addition of other compounds employable in the method.

It is yet another object of the present invention to provide such a method which effects rapid penetration of the wood preservatives into the wood.

It is another object of the invention to provide such a method which involves heating at least one of (a) the wood prior to treatment, (b) the solution and (c) the treated wood.

It is another object of the present invention to provide such a method which is usable on a wide variety of types of wood and resists undesired grain raising.

It is yet another object of the present invention to employ a buffering agent in an amount effective for the desired buffering, but preferably not in the higher amount needed for the buffering agent to function as a preservative.

These and other objects of the invention will be more fully understood from the following description of the invention on reference to the illustration appended hereto.

BRIEF DESCRIPTION OF THE DRAWINGS

The FIGURE is a schematic illustration of a cross-section of a portion of a wood sample.

DESCRIPTION OF THE PREFERRED EMBODIMENTS

As employed herein, the term "buffering agent" means boric acid, borax, disodium octaborate, phosphates, calcium phosphates, calcium hydroxide, as well as other effective buffering materials and combinations thereof.

As employed herein, "wood" means wood, wood-based materials, wood fiber materials, forest products, timber, lumber, engineered wood, millwork, joinery, wood laminates, laminated veneer lumber, plywood, laminated strand lumber, wood fiber composites, medium density fiberboard, particle board, hard board, oriented strand board, wood fiber resin composites, wood strand resin composites, wood particle resin composites and other wood and wood fiber-based materials and fabricated and semi-fabricated items made therefrom As employed herein, the term "wood preservatives" means organic compounds, halo-organic compounds, metalo-organic compounds, organo-salts, borates, organophosphates and non-organoboron compounds having fungicidal, insecticidal, water-resistant, termite-resisting, decay-resisting, stain-resisting or other wood-protective properties.

As used herein, the term "amine oxide" or "amine oxide compound" refers to those compounds which are formed as reaction products in the reaction of tertiary amines and hydrogen peroxides and are represented by the general formula:

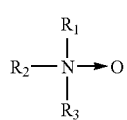

$$R_2 \!-\! \underset{\underset{R_3}{|}}{\overset{\overset{R_1}{|}}{N}} \!\to\! O \qquad (1)$$

where $R_1$, $R_2$ and $R_3$ are independent and can be a linear, branched, cyclic, aromatic or any combination thereof of saturated or unsaturated C1 to C20 group and any C2-C20 carbon atom can be replaced with a hetero-atom selected from the group consisting of O, S and N.

Preferred amine oxides are alkyl dimethyl amine oxides such as decyl dimethyl amine oxide, lauryl dimethyl amine oxide, isoalkyl dimethyl amine oxide, myristyl dimethyl amine oxide, cetyl dimethyl amine oxide, stearyl dimethyl amine oxide and octyl dimethyl amine oxide. Most preferred is N-alkyl (C12-C16)-N,N-dimethylamine oxide (ADO).

In a preferred method of the present invention, a solution contains one or more amine oxides along with a buffering agent and at least one wood preservative with the solution having a pH of about 5 to 12.4 and preferably about 7 to 10 and most preferably about 7 to 8.5.

Below a pH of 7, the maximum penetration effectiveness is not achieved and above a pH of 10, the wood properties may be damaged. Natural woods have a pH in the acid range. For example, oaks, Douglas fir, aspen and pines have pH's in the range of about 4.0 to 5.5.

A wide variety of amine oxides in the context of wood preservation have been known. See, for example, U.S. Pat. Nos. 6,340,384; 6,375,727; 6,416,789; 5,833,741; 6,527,981; 6,572,788; 6,508,869 and U.S. patent application Ser. No. 10/351,021, which became United States Published Patent Application 20040248973, now U.S. Pat. No. 7,056,919, the disclosures of which is expressly incorporated herein by reference.

If desired, the materials may be provided in concentrate form in a solution of a suitable solvent, such as water, with the final solution to be applied being created by adding additional solvent and mixing the same in order to minimize shipping and storing of the solvent volume required to make up the difference between the concentrate solvent volume and the final solution solvent volume.

The solution preferably contains about 0.11 to 70 weight percent of one or more amine oxides and most preferably about 1 to 20 weight percent. The buffering agent is present in about 3 to 80 weight percent and preferably about 5 to 30 weight percent, all based on weight of total solution. The wood preservative is present in about 3 ppm to 50 weight percent based on weight of total solution and preferably about 20 ppm to 5,000 ppm. The solution is in water or another suitable solvent such as ethanol or ethylene glycol, for example.

The materials may be provided in the form of a concentrate which will be diluted prior to application to achieve the foregoing relationships.

The solution is applied to the wood by any desired means such as spraying, rolling on or dipping, for example. If desired, amounts of pressure or vacuum without totally filling the wood with liquid could be employed. The wood so treated may be stored for a period of time before activation or may be activated promptly thereafter by treatment at an elevated temperature in a high relative humidity environment. Application may be achieved at any temperature between ambient and boiling temperature, but in the preferred approach to the invention, the application will be achieved at a temperature of about 30 to 75° C. and preferably at a temperature of about 50 to 60° C. Activation is preferably achieved over a period of at least 8 hours at ambient temperature to steam temperature and preferably at about 70 to 95° C. and at a relative humidity of about 60 to 100% and preferably about 80 to 100%. It is preferred to preheat the wood to about 8° C. to 230° C. and most preferably at about 12° C. to 100° C.

In one preferred embodiment, the buffering agent may comprise about 50 to 60 weight percent borax and about 40 to 50 weight percent boric acid.

It will be appreciated that more than one buffering agent, amine oxide or wood preservative may be employed and the ranges set forth herein refer to each category with a single compound or a combination of compounds.

The balance of the solution may be a suitable solvent such as water, ethanol or ethylene glycol, for example, or any desired additives such as water repellants, waxes, such as paraffin wax, for example, polymers, silicones and combinations thereof. A suitable wax-polymer emulsion is that sold under the trademark WRS-3 by Kop-Coat, Inc.

If desired, a suitable coloring agent such as an iron oxide pigment dispersion, red dye or phantom blue dye as offered under the trade designation Day Glo or others may be employed.

If desired, glycols and other additives which help solubilize materials such as the buffering agent, amine oxides, wood preservatives, water repellants and the like may be employed.

Also, additives such as glycols and alcohols which serve as solvents and may be employed in quantities of about 5 to 40 weight percent based on total solution. Among the suitable glycols are ethylene glycol, propylene glycol or polyethylene glycol.

The process has been found to provide deeper and more rapid penetration than processes which do not employ a solution as disclosed hereinabove. Enhanced performance is achieved by applying heat to the wood before or after application or to the solution or by combinations thereof. The solution also may be applied without requiring prior art pressure impregnation or the use of vacuum conditions or undesirable, potentially health-hazardous and environmentally undesirable volatile solvents such as petroleum distillates.

Among the wood preservatives usable in the present invention are 3-iodo-2-propynyl butyl carbamate (IPBC), diiodomethyl-p-tolylsulfone (DIMPTS), halogenated organics, azoles, quaternary ammonium compounds, isothiazalones, metallic organics, borates, copper naphthenate, copper oxide, tributyltin oxide, zinc omadine, salts of organics and metallorganics. The amount of these wood preservatives to be employed will be well known to those skilled in the art with the two additional compounds of the present invention expediting the rate of penetration into the wood. Within this group, insecticides such as synthetic pyrethroids, nicotinimides, organophosphates, phenylpyrazoles and others, for example, may be employed. Among the suitable insecticides are at least one material selected from the group consisting of nicotinimides, synthetic pyrethroids, borates and combinations thereof. Those skilled in the art will know the conventional quantities of the insecticides which may be employed.

Fungicides such as chlorothalonil, 2-(thiocyanomethylthio)benzothiazole (TCMTB), methylene bisthiocyanate, bethoxazins, DIMPTS (diiodomethyl-p-tolylsulfone), IPBC (3-iodo-2-propynyl butyl carbamate), triazoles, borates, isothiazalones, phenols, quaternary ammonium compounds and combinations thereof and others, for example, may be employed. Those skilled in the art will know well the conventional quantities of fungicides to be introduced into the wood.

It will be appreciated that when a plurality of wood preservatives are employed in the process of the present invention, different preservatives may penetrate to different depths of the wood than others. Also, depending upon the wood and its inherent wood pH and other characteristics of a specific wood and target penetration, it may be desirable within the range to modify the pH of the solution.

In another approach to the invention, the wood to which the solution has been applied may be stacked and penetration attained by wrapping the warm, freshly coated sub-straight stacks in an air-impervious material such as a suitable resinous plastic sheet and allowing it to stand at ambient temperature for 8 hours to three days. Additional penetration may be achieved thereafter through the activation process.

Another benefit of the present invention is that the wood surface appears to be clean and dry with no substantial undesirable grain raising.

The method of the present invention may be practiced in an in-line manner to process the wood efficiently while avoiding undesired forces such as would exist in pressurized treatment which may cause a straight board to depart from its desired straight configuration.

The wood may also be engineered wood or laminated wood having a glued layer or substantial amount of glue therein with the method effecting penetration of the wood preservative through the glue.

The method may be performed on wood with any amount of moisture content including green (wet) wood and on wood which has moisture at a level which does not exceed the fiber saturation point of the wood and on dry wood.

EXAMPLES

In order to provide an enhanced understanding of the invention, examples will be provided.

Example 1

Chemical component mixtures as shown in Table 1 were heated to 60° C. using an in-line recirculating heater. The hot mixtures were stirred until homogenous. Radiata Pine lumber of dimensions approximately 45 mm deep, 90 mm wide and 3,000 mm long were immersed for 1 second in one of the hot mixtures. Before treatment, the Radiata Pine lumber had oven dry moisture content ranging from 9 to 15% by weight; each piece weighed between 4,800 grams and 5,300 grams. The one-second immersion applied between 70 grams and 100 grams of mixture to each piece of lumber. Five pieces of lumber were immersed in mixtures of 50 to 60° C. The mixtures were allowed to cool to 30 to 40° C. before a second set of 5 samples was immersed. After treatment, the lumber was stored for 6 hours. Different treatment sets were separated during storage. After 6 hours at ambient room temperature and humidity, each piece of lumber was stored under Condition #1 shown in Table 1, while the other half was stored under Condition #2 shown in Table 2. After 24 hours of exposure to either Condition #1 or #2, the samples were cut and tested for the depth of penetration using the New Zealand Standard Curcumin test. The results of the tests (Table 3) show the unusually deep penetration of mixtures that contain a buffer and an amine oxide. In this case, the buffer, a boron compound, is also known to have rot and decay inhibiting properties. In general, an average wood sample penetration in percent depth at 75 or above would provide the desired inhibition properties. For example, Mixture III in the column for "Storage Condition 2" at both temperature ranges A and B produces successful penetration. Considering the Compositions III and V as compared with Composition IV, it will be appreciated that the amine oxide and boric buffer quantities were identical with a prime difference being that in IV, glycol provided 40% of the total of 58% solvent confirming the use of glycol as a solvent and not for another purpose. Considering Table 3, it will be seen that the results for Composition IV wherein glycol substituted for a significant portion of the water as the solvent, the results were not as good as Compositions III and V. Analytical confirmation using the New Zealand Standard Extraction and Titration Method (Table 4) shows the correlation with the Curcumin test results. In this case, the buffer, a borate compound, has penetrated to the center zone of the lumber. The analyses also confirmed that the boron compounds were present in the center zone at concentrations known to provide inhibition of decay and rot fungi. In the column labeled "Detectable Boron", the word "No" indicates that boron concentration within the zone of 66 to 100% penetration to the center of the wooded sample did not exceed 0.01% by weight. If the word "Yes" appears adjacent a mixture in that column, it means that the boron concentration did exceed 0.01% by weight and was present in sufficient quantities to inhibit rot/decay. Treated lumber samples were also stored for 7 months in a plastic bag. During storage, mold grew on the cross-sectional surfaces of all samples. The percentages contained in the last column of Table 5 refer to the percent of the exposed cross-sectional area of the sample. This will generally relate to depth so that a "0" in this column means that the cross-sectional—exposed end of the sample was 100% covered in mold and the number "50" means that 50% of the sample was covered with mold. The samples treated with the mixture containing fungicides in combination with the buffered amine oxide showed surprising mold resistance to a depth of 50% of the depth to the center (Table 5). This result confirms that at least one of the fungicides was also carried unusually deep into the wood by the buffered amine oxide mixture.

The results in Tables 3, 4 and 5 also show the unexpected extreme penetration benefit of heating the buffered amine oxide mixtures and/or heating the buffered amine oxide-treated wood while maintaining high relative humidity.

TABLE 1

Mixtures

| Mixtures | Component | Proportions - Percent by Weight - |
|---|---|---|
| I | Water | 60.00 |
|  | Borate Buffer | 40.00 |
| II | Water | 20.00 |
|  | Borate Buffer | 40.00 |
|  | Glycol | 40.00 |
| III | Water | 58.00 |
|  | Amine Oxide | 2.00 |
|  | Borate Buffer | 40.00 |
| IV | Water | 18.00 |
|  | Amine Oxide | 2.00 |
|  | Borate Buffer | 40.00 |
|  | Glycol | 40.00 |
| V | Water | 53.00 |
|  | Amine Oxide | 2.00 |
|  | Borate Buffer | 40.00 |
|  | Water Repellent | 5.00 |
| VI | Water | 33.00 |
|  | Amine Oxide | 2.00 |
|  | Borate Buffer | 40.00 |
|  | Glycol | 20.00 |
|  | Water Repellent | 5.00 |
| VII | Water | 56.00 |
|  | Amine Oxide | 2.00 |
|  | Borate Buffer | 40.00 |
|  | Fungicide (IPBC) | 0.15 |
|  | Fungicide (DDAC) | 1.30 |
|  | Fungicide Cosolvent | 0.55 |
| VIII | Water | 58.00 |
|  | Borate Buffer | 40.00 |
|  | Fungicide (IPBC) | 0.15 |
|  | Fungicide (DDAC) | 1.30 |
|  | Fungicide Cosolvent | 0.55 |

Note:
Buffer Borate = Disodium Octaborate Tetrahydrate
Glycol = Propylene Glycol
Amine Oxide = N-Alkyl ($C_{12}$-$C_{16}$) dimethyl amine oxide
Water Repellent = WRS-3 ™ Breathable Barrier
Fungicide (IPBC)/DDAC/Cosolvents = NP-1 ® Sapstain Control Product

TABLE 2

Treated Wood Storage Conditions

| 24-Hour Storage Condition* | Relative Humidity - % - | Temperature - C. ° - |
|---|---|---|
| I | 65 to 80 | 18 to 25 |
| II | 95 to 100 | 80 to 98 |

Note:
*All samples were stored for 6 hours after treatment before 24-hour storage conditions were started.

TABLE 3

Penetration of Wood

| | | Average Wood Sample Penetration* in Percent Depth Storage Condition | |
|---|---|---|---|
| Mixture | Mixture Temperature - C. ° - | 1 - % - | 2 - % - |
| I | A. 30 to 40° C. | 10 | 15 |
|  | B. 50 to 60° C. | 15 | 20 |
| II | A. 30 to 40° C. | 20 | 25 |
|  | B. 50 to 60° C. | 25 | 25 |
| III | A. 30 to 40° C. | 25 | 75 |
|  | B. 50 to 60° C. | 50 | 100 |
| IV | A. 30 to 40° C. | 20 | 40 |
|  | B. 50 to 60° C. | 40 | 70 |
| V | A. 30 to 40° C. | 30 | 80 |
|  | B. 50 to 60° C. | 55 | 100 |
| VI | A. 30 to 40° C. | 30 | 80 |
|  | B. 50 to 60° C. | 55 | 100 |
| VII | A. 30 to 40° C. | 25 | 80 |
|  | B. 50 to 60° C. | 55 | 100 |
| VIII | B. 50 to 60° C. | 15 | 20 |

*Average of 5 Samples:
Depth of penetration determined using New Zealand Standard Curcumin indicator for boron. Penetration measured in the center of the 43 to 45-mm thick sample (100% penetration is 22 mm to reach the center).

TABLE 4

Analyses to Confirm Penetration to Rot/Decay Inhibition Levels
Treated Wood Samples

| Mixture | Mixture Temperatures | Storage Condition | Detectable Boron* From Depth Zone 66% to 100% |
|---|---|---|---|
| I | A | 1 | No |
| I | A | 2 | No |
| I | B | 1 | No |
| I | B | 2 | No |
| II | B | 2 | No |
| III | A | 2 | Yes |
| III | B | 2 | Yes |
| IV | B | 2 | Yes |
| V | A | 2 | Yes |
| VI | A | 2 | Yes |
| VII | A | 2 | Yes |
| VIII | B | 2 | No |

*Boron as (BAE) greater than or equal to 0.01% by weight as determined by New Zealand Standards Titration analysis.
Note:
0.01% BAE is recognized as the minimum inhibiting concentration required to inhibit rot/decay spore germination and/or growth in standard tests.

TABLE 5

Penetration of Mold Inhibitor Fungicides
Treated Wood Samples

| Mixture | Mixture Temperature | Storage Condition | Average Mold Inhibition * Percent Depth |
|---|---|---|---|
| I | A | 1 | 0 |
| I | A | 2 | 0 |
| I | B | 1 | 0 |
| I | B | 2 | 0 |
| II | B | 2 | 0 |
| III | A | 2 | 0 |
| III | B | 2 | 0 |
| IV | B | 2 | 0 |
| V | A | 2 | 0 |

TABLE 5-continued

Penetration of Mold Inhibitor Fungicides Treated Wood Samples

| Mixture | Mixture Temperature | Storage Condition | Average Mold Inhibition * Percent Depth |
|---|---|---|---|
| VI | A | 2 | 0 |
| VII | A | 2 | 50 |
| VIII | B | 2 | 5 |

* Average of 5 samples. Treated Radiata Pine samples stored at ambient temperatures 1 to 29° C. and 65 to 100% RH in a plastic bag for 7 months.

Example 2

The chemical component mixtures shown in Table 1 were stirred until homogenous. The temperature of the mixture was 30° C. Aspen and Southern Yellow Pine-oriented Strand Board (OSB) with commercial specifications of "7/16-inch thickness" heated to 120° to 140° C. was sprayed with the chemical component mixtures. Additional ambient temperature OSB was also sprayed. The spray applied between 30 and 35 grams of mixture per 1,000 square centimeters of OSB. After the spray was applied, the OSB was stacked. The stacks gradually cooled to room temperature after 24 hours. The OSB board was cut into three depth zones according to FIGURE. Each cut face was tested for the presence of borate buffer using the standard curcumin test. Samples of zones that tested positive for borate buffer were grouped up in a Wylie mill. Ground sample was analyzed for iodine to determine the concentration of IPBC fungicide using an x-ray fluorescence spectrometer. Ground sample was also extracted and then analyzed for nicotinimide insecticide using high pressure liquid chromatography. Additional ground sample was digested and then analyzed for boron to determine the concentration of borate buffer using an inductively coupled plasma spectrometer. The results of the analyses are shown in Table 7 with reference to the FIGURE. The results show the unexpected penetration of the borate buffer as well as the organic insecticide (nicotinimides) and the fungicide (IPBC).

The study was duplicated. The results are also shown in Table 7. The duplicate study included two types of nicotinimides. Both nicotinimides penetrated with the buffered amine oxide mixture.

Referring to the FIGURE, there is represented in fragmentary fashion a 7/16-inch wood specimen with the zones delineated with the numbers 1, 2 and 3 with increasing numbers referring to regions closer to the center of the wood specimen.

The study was repeated again; this time, the Disodium Octaborate buffer was replaced with a mixture of sodium borate pentahydrate and the boric acid in a ratio of 1.17:1.00. In addition, this study included a mixture with about 40% less buffer (on a BAE basis) and about 80% less amine oxide. (See Table 6, Mixture V.) The results show greatly enhanced penetration. Also, the mixture was heated to 60° C. and the mixture was applied in a commercial OSB plant manufacturing Southern Yellow Pine OSB. The OSB was 120° to 140° C. hot from the OSB manufacturing process. The mixture was applied by in process, in-line spray to apply 7 gallons per thousand square feet of 7/16-inch OSB board. Results of the penetration tests are shown in Table 7. Results show greatly enhanced penetration. The treated Southern Yellow Pine OSB was exposed to standard Formosan termite and fungal tests. Preservative performance was compared to untreated and 100%-treated controls to determine relative performance.

The borate buffer provided some inherent termite and decay resistance. Mixtures with the amine oxide, however, provided much greater performance due to enhanced penetration. Mixtures with the buffered amine oxide with insecticides provided the best performance due to the penetration of the insecticides. Analyses (ICP method) showed that borate levels in Zone 3 were as high as 0.34% per weight on a BAE basis. Published historical data shows that Zone 3 would need to contain 0.75 to 1.15% BAE to prevent termite feeding in that zone.

It can be concluded that the penetration of insecticides extend to Zone 3 even though analyses can only confirm penetration to Zone 2.

It should also be noted that the termite attack centered on Zone 3 in all cases where attacks occurred. This further shows the enhanced penetration of the borate and insecticide in the buffered amine oxide mixture.

TABLE 6

Mixture

| Mixtures | Component | Proportions - Percent by Weight - |
|---|---|---|
| I | Water | 97.47 |
|   | Amine Oxide | 0.60 |
|   | Fungicide (IPBC) | 0.18 |
|   | Fungicide (IST) | 0.01 |
|   | Cosolvent for Fungicides | 0.74 |
|   | Surfactant | 1.00 |
| II | Water | 80.00 |
|   | Borate Buffer A* | 20.00 |
| III | Water | 79.40 |
|   | Borate Buffer A* | 20.00 |
|   | Amine Oxide | 0.60 |
| IV | Water | 77.54 |
|   | Borate Buffer A* | 20.00 |
|   | Amine Oxide | 0.60 |
|   | Fungicide (IPBC) | 0.18 |
|   | Fungicide (IST) | 0.01 |
|   | Insecticide (Nicotinimide) | 0.01 |
|   | Insecticide (Synthetic Pyrethroid) | 0.02 |
|   | Cosolvent for Fungicide | 0.64 |
|   | Surfactant | 1.00 |
| V | Water | 83.82 |
|   | Borate Buffer B | 8.30 |
|   | Borate Buffer C | 7.08 |
|   | Amine Oxide | 0.11 |
|   | Fungicide (IPBC) | 0.03 |
|   | Fungicide (IST) | <.01 |
|   | Insecticide (Nicotinimide) | 0.03 |
|   | Insecticide (Synthetic Pyrethroid) | 0.01 |
|   | Cosolvent for Fungicides | 0.39 |
|   | Surfactant | 0.22 |

*Borate Buffer A = Disodium Octaborate (23.4% BAE)
*Borate Buffer B = Sodium Borate Pentahydrate (7.06% BAE)
*Borate Buffer C = Boric Acid (7.08% BAE)
**B + C = 14.16% BAE

TABLE 7

Results of Wood Penetration Analysis

| Mixture | Board Condition | Mixture Component | Analyses[1] | Analytical Penetration Zone | Biological Test Results Percent Protection[3] | | Biological Protection vs. Penetration |
|---|---|---|---|---|---|---|---|
| | | | | | Formosan Termites[4] | Rots Decays[5] | |
| I | Hot | IPBC Fungicide | X-ray | 1 | | 20 | Surface treatment No penetration |
| II | Hot | Borate | Curcumin | 1 | 30 | 50 | Surface treatment Some natural diffusion of borate |
| III | Hot | Borate | Curcumin | 3 | 75 | 100 | Deep penetration borate alone sufficient for decay, but insufficient for termites |
| III | Ambient | Borate | Curcumin | 2 | 75 | 100 | Penetration sufficient for decay, but insufficient for termites |
| IV | Hot | Borate | Curcumin | 3 | 3 | 100/100 | 100/100 | Penetration of insecticides sufficient to provide termite protection |
| | | Borate | ICP | 3 | 3 | | | |
| | | IPBC Fungicide | X-ray | 3 | 3 | | | |
| | | Nicotinimide | HPLC | 2 | 2[2]* | | | |
| V | Hot/Fresh | Borate | Curcumin | 3 | | 100 | 100 | Penetration/Performance |

[1] Presence confirmed at levels above background for each component and method
[2] The Duplicate Series included two separate nicotinimides.
[3] Percent protection is reported in comparison to treated and untreated controls.
[4] AWPA Standard Test
[5] EN 113 adapted Referring in Table 7 to the heading entitled "Biological Protection vs. Penetration", the Mixture I specimen experienced rotting in Zones 2 and 3 and termite attack in Zones 1, 2 and 3. The Mixture II showed rot in Zone 3 and termite attack in Zone 3.

Mixture III showed no rot and termite attack only in Zone 3. Mixture III (hot condition) showed that Mixture III (ambient condition) showed no rot and termite attack in Zones 2 and 3, thereby showing the benefit of heating of the wood. Mixture IV showed no rot and no termite attack. Mixture V also showed no rot and no termite attack.

Cross-sectional analysis of treated boards showed substantial penetration of key ingredients, especially the borate component.

From these examples, it can be seen that treatment utilizing the solutions and process outlined in this invention imparts no significant discoloration or grain-raising to treated lumber. Moreover, surface treatment following this invention allows for penetration of active ingredients into lumber without the need for pressure or double vacuum treatments.

It will be appreciated, therefore, that the method of the present invention provides an efficient, safe, economically feasible method of rapidly and effectively causing deep penetration of wood preservatives as a result of the unique solution and the combination of buffering agent and amine oxide. All of this is accomplished without requiring pressure impregnation, the use of vacuum conditions and the use of health and environmentally undesirable solvents.

Whereas particular embodiments of the invention have been described herein for purposes of illustration, it will be evident to those skilled in the art that numerous variations of the details may be made without departing from the invention as set forth in the appended claims.

The invention claimed is:

1. A wood preservative solution comprising
   at least one amine oxide,
   at least one wood preservative and a buffering agent with the balance being at least one suitable solvent,
   said solution having a pH of about 7 to 10, and
   said buffering agent being present in a sufficiently small amount that it does not provide a substantial wood preservation effect, whereby the interaction of the amine oxide with the buffering agent will have a synergistic effect to effect a greater depth of penetration of said wood preservative.

2. The solution of claim 1 including
   employing water as said solvent.

3. The solution of claim 1 including
   said amine oxide being selected from the group of alkyl dimethyl amine oxides, decyl dimethyl amine oxide, lauryl dimethyl amine oxide, isoalkyl dimethyl amine oxide, myristyl dimethyl amine oxide, cetyl dimethyl amine oxide, stearyl dimethyl amine oxide, octyl dimethyl amine oxide and N-alkyl(C12-C16)-N,N-dimethylamine oxide (ADO) and combinations thereof.

4. The solution of claim 1 including
   employing said buffering agent in an amount of about 3 to 80 weight percent based on total solution weight.

5. The solution of claim 4 including
   employing said amine oxide in an amount of about 0.11 to 70 weight percent based on total solution weight.

6. The solution of claim 5 including
   employing said wood preservative in an amount of about 3 ppm to 50 percent based on total solution weight.

7. The solution of claim 5 including
   employing said amine oxide in a weight percent of about 1 to 20 percent of said solution.

8. The solution of claim 1 including
   employing said buffering agent in a weight percent of about 5 to 30 percent of said solution weight.

9. The solution of claim 1 including employing as said solution a solution having a pH of about 7 to 8.5.

10. The solution of claim 1 including employing at least one solvent additive in said solution.

11. The solution of claim 10 including said solvent additive selected from the group consisting of glycols, alcohols and combinations thereof.

12. The solution of claim 10 including a water repellent being present as a said additive.

13. The solution of claim 12 including said water repellent including a wax-polymer emulsion.

14. The solution of claim 1 including said wood preservative being present in amount of about 20 ppm to 5000 ppm.

15. The solution of claim 14 including said wood preservative including at least one fungicide.

16. The solution of claim 15 including said fungicide selected from the group consisting of 3-iodo-2-propynyl butyl carbamate, diiodomethyl-p-tolylsulfone, triazoles, isothiazalones, phenols, quaternary ammonium compounds and combinations thereof.

17. The solution of claim 14 including said wood preservatives including at least one insecticide.

18. The solution of claim 17 including said insecticide including at least one material selected from the group consisting of nicotinimides, pyrethroids and combinations thereof.

19. The solution of claim 1 including said wood being a wood selected from the group consisting of engineered wood and laminated wood having a glued layer or substantial amount of glue therein.

20. A wood preservative solution comprising
at least one amine oxide,
at least one wood preservative and a buffering agent with the balance being at least one suitable solvent, and
said buffering agent about 50 to 60 weight percent borax and about 40 to 50 weight percent boric acid.

* * * * *

UNITED STATES PATENT AND TRADEMARK OFFICE
CERTIFICATE OF CORRECTION

Page 1 of 2

PATENT NO.        : 7,896,960 B2
APPLICATION NO.   : 12/236044
DATED             : March 1, 2011
INVENTOR(S)       : Hans A. Ward et al.

It is certified that error appears in the above-identified patent and that said Letters Patent is hereby corrected as shown below:

Title page, second column, *Primary Examiner* - "Anthony J Green" should read --Anthony J. Green--.
Column 1, line 47, "woods materials" should read --wood materials--.
Column 2, line 43, "i.e. lum-" should read --i.e., lum- --.
Column 3, line 26, "from" should read --from.--.
Column 3, line 66, "pH's" should read --pHs--.
Column 4, line 55, "repellants" should read --repellents--.
Column 4, line 65, "repellants" should read --repellents--.
Column 5, line 14, "diiodom-" should read --diiodo- --.
Column 5, line 15, "ethyl-p-tolylsulfone" should read --methyl-p-tolylsulfone--.
Column 8, line 47 (Table 4), "Standard Titration Method analysis." should read --Standard Extraction and Titration Method analysis.--
Columns 11 and 12, Table 8, the heading for the fifth column of the Table, Analytical Penetration
"    Zone    "

should read

Analytical
      Penetration
--   Zone   --.

Signed and Sealed this
Thirty-first Day of July, 2012

David J. Kappos
*Director of the United States Patent and Trademark Office*

Columns 11 and 12, Table 8, the headings for the sixth and seventh columns of the Table, Biological Test Results
   Percent Protection [3]

Formosan  Rots
 " Termites[4]  Decays[5] "

should read

Biological Test Results
   Percent Protection [3]
   Formosan  Rots
 -- Termites[4]  Decays[5] --.

Column 13, line 14, "in amount" should read --in an amount--.